United States Patent
Farrell et al.

(10) Patent No.: US 12,201,750 B2
(45) Date of Patent: Jan. 21, 2025

(54) HYDRATION SOLUTIONS CONTAINING VOLATILE SOLUTIONS AND MEDICAL DEVICE PRODUCTS INCLUDING THE SAME

(71) Applicant: Hollister Incorporated, Libertyville, IL (US)

(72) Inventors: David J. Farrell, Ballina (IE); Kevin Murnaghan, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 177 days.

(21) Appl. No.: 17/294,316

(22) PCT Filed: Nov. 20, 2019

(86) PCT No.: PCT/US2019/062365
§ 371 (c)(1),
(2) Date: May 14, 2021

(87) PCT Pub. No.: WO2020/106812
PCT Pub. Date: May 28, 2020

(65) Prior Publication Data
US 2022/0008626 A1    Jan. 13, 2022

Related U.S. Application Data

(60) Provisional application No. 62/770,294, filed on Nov. 21, 2018.

(51) Int. Cl.
*A61L 29/08* (2006.01)
*A61L 29/10* (2006.01)

(52) U.S. Cl.
CPC .......... *A61L 29/085* (2013.01); *A61L 29/106* (2013.01); *A61L 2400/10* (2013.01)

(58) Field of Classification Search
CPC . A61M 25/002; A61K 31/375; A61K 31/785; A61L 29/041; A61L 29/085; B05D 1/62; A61P 31/04; C10M 173/00
See application file for complete search history.

(56) References Cited

U.S. PATENT DOCUMENTS 4,941,308 A * 7/1990 Grabenkort ......... A61M 25/002
                                                    53/445
6,634,498 B2   10/2003  Kayerod et al.
7,615,045 B2   11/2009  Israelsson et al.
8,671,647 B2   3/2014   Boothe et al.
(Continued)

FOREIGN PATENT DOCUMENTS

EP    2072075 A1    6/2009
JP    2001130634 A  5/2001
(Continued)

OTHER PUBLICATIONS

Whitehead, Dissolved Gases in Purified Water, May 2023, ELGA LabWater, pp. 1-14 (Year: 2023).*
"Mohamed and Eastoe," "How can we use carbon dioxide as a solvent," School Science Review, vol. 93, Dec. 2011, https://s3.amazonaws.com/academia.edu.documents/7098472/SSR%20December%202011%20073-080%20Mohamed%20%20Eastoe.pdfAWSAccessKeyId=AKIAIWOWYYGZ2Y53UL3A Expires=1534568825Signature=JNTr2%2FOCpMsKW9Wgt7gls%2Bku8Mg%3D response-contentdisposition=inline%3B%20filename%3DHow_can_we_use_carbon_dioxide_as_a_solve.pdf.
(Continued)

*Primary Examiner* — Dah-Wei D. Yuan
*Assistant Examiner* — Andrew J Bowman
(74) *Attorney, Agent, or Firm* — Cook Alex Ltd.

(57) ABSTRACT

Hydration solutions including a liquid and a volatile solute, assemblies containing hydration solutions and methods of making the same.

22 Claims, 3 Drawing Sheets

(56) References Cited

U.S. PATENT DOCUMENTS

| | | |
|---|---|---|
| 8,900,651 B2 | 12/2014 | McClain et al. |
| 9,033,149 B2 | 5/2015 | Terry |
| 2005/0137582 A1 | 6/2005 | Kull-Osterlin et al. |
| 2005/0214443 A1 | 9/2005 | Madsen |
| 2007/0009582 A1 | 1/2007 | Madsen et al. |
| 2008/0177373 A1 | 7/2008 | Huang et al. |
| 2014/0342954 A1 | 11/2014 | Ingber et al. |
| 2015/0258247 A1 * | 9/2015 | Rostami .............. A61L 29/041 523/105 |
| 2016/0213880 A1 | 7/2016 | Oflynn et al. |
| 2020/0352991 A1 * | 11/2020 | Modak .............. A61K 31/375 |

FOREIGN PATENT DOCUMENTS

| | | | | |
|---|---|---|---|---|
| WO | WO-2007062306 A2 * | 5/2007 | ............. | A01N 25/24 |
| WO | WO-2015085040 A1 * | 6/2015 | ......... | A61B 5/14532 |
| WO | WO-2017089739 A1 * | 6/2017 | ........... | A61L 29/085 |
| WO | WO-2019222644 A1 * | 11/2019 | ........... | A61L 29/043 |

OTHER PUBLICATIONS

Whitehead et al. (Year: 2023).*

Nunes and Duarte, "Dense CO2 as a Solute, Co-Solute or Co-Solvent in Particle Formation Processes: A Review," Materials, vol. 4, Nov. 2011, https://www.ncbi.nlm.nih.gov/pmc/articles/PMC5448852/pdf/materials-04-02017.pdf.

Kim, "Deposition of Thin Organic and Metal Films from Carbon Dioxide by Free Meniscus and Solvent Displacement Methods," Jun. 2005, https://repository.lib.ncsu.edu/handle/1840.16/5708.

Flinn Scientific, "Quick Freeze: Saturated, Unsaturated, and Supersaturated Solutions," 2016, https://www.flinnsci.com/api/library/Download/69e2317313094ff08a9d98db7a855c49.

International Search Report and Written Opinion for International Application No. PCT/US2019/062365, dated Mar. 13, 2020.

* cited by examiner

HYDRATION SOLUTIONS CONTAINING VOLATILE SOLUTIONS AND MEDICAL DEVICE PRODUCTS INCLUDING THE SAME

The present application is the U.S. National Stage Application of PCT Application No. PCT/US2019/062365, filed Nov. 20, 2019, which claims the benefit and priority of U.S. Provisional Patent Application No. 62/770,294, filed Nov. 21, 2018, both of which are hereby incorporated herein by reference.

DESCRIPTION

Technical Field

The present disclosure generally relates to hydration solutions for hydrating or wetting a device. More particularly, the present disclosure generally relates to liquid hydration solutions that contain volatile solutes and assemblies that contain the same. The present disclosure also generally relates to medical device products that contain such hydration solutions, and methods of making such solutions and medical device products.

Background

Several different devices in different industries are required to be hydrated prior to use and/or stored in a hydrated condition. In several instances, such devices are stored or packaged in a hydration medium, such as a liquid hydration medium. Liquid hydration mediums may be, but are not limited to, water or aqueous solutions.

One type of device wherein it may be advantageous to package the device in a hydrated stated and/or in a hydration medium is a medical device that is made from a hydrophilic material, such as a hydrophilically coated urinary catheter. In several applications, a coating of hydrophilic material is applied to the surface of a device to provide a lubricious surface. When the hydrophilic material is wetted or hydrated with a hydration medium, the hydrophilic material becomes extremely lubricous. The hydration medium may be, for example, liquid water or an aqueous solution. In the field of insertable medical devices, the lubriciousness of the hydrophilic coating can ease introduction of the device into the body and aids in reducing pain and discomfort associated with such introduction.

In devices that are required to be stored in and/or hydrated with a hydration medium, the device may be packaged with the hydration medium, such that the device is in contact with the hydration medium. In such packaged products, the hydration medium hydrates the device.

In the field of intermittent hydrophilic urinary catheters, the package may contain the urinary catheter and hydration liquid wherein the liquid is in contact with and hydrates the hydrophilic material of the catheter. Such catheters are used for self-catheterization about five to six times a day. Thus, the user may carry a supply of catheters with them. If the user is in a colder climate, the packaged catheters may be exposed to cold temperatures. Exposure to colder temperatures may cause the water within the package and within hydrophilic coating to freeze. Such freezing of the water may degrade or cause issues with the hydrophilic material of the catheter.

Therefore, there remains a need for improved hydration mediums for packaged medical device products and methods of hydrating devices within a package and/or packaging a device with a hydration medium.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a hydration medium for hydrating or wetting a device. The hydration medium comprising a solution including a liquid and a volatile solute dissolved in the liquid.

In another aspect, a packaged device including a package containing the device and a hydration medium comprising a solution including a liquid and a volatile solute dissolved in the liquid.

In yet another aspect, a method of making a urinary catheter product. The method includes placing a hydrophilic catheter within a package. A first component and a second component are dispensed into the package. The first component and the second component are combined to produce a hydration solution including a liquid and a volatile solute dissolved in the liquid, wherein the hydration solution wets hydrates a hydrophilic material of the hydrophilic catheter.

DETAILED DESCRIPTION OF THE ILLUSTRATED EMBODIMENTS

Figure 1:
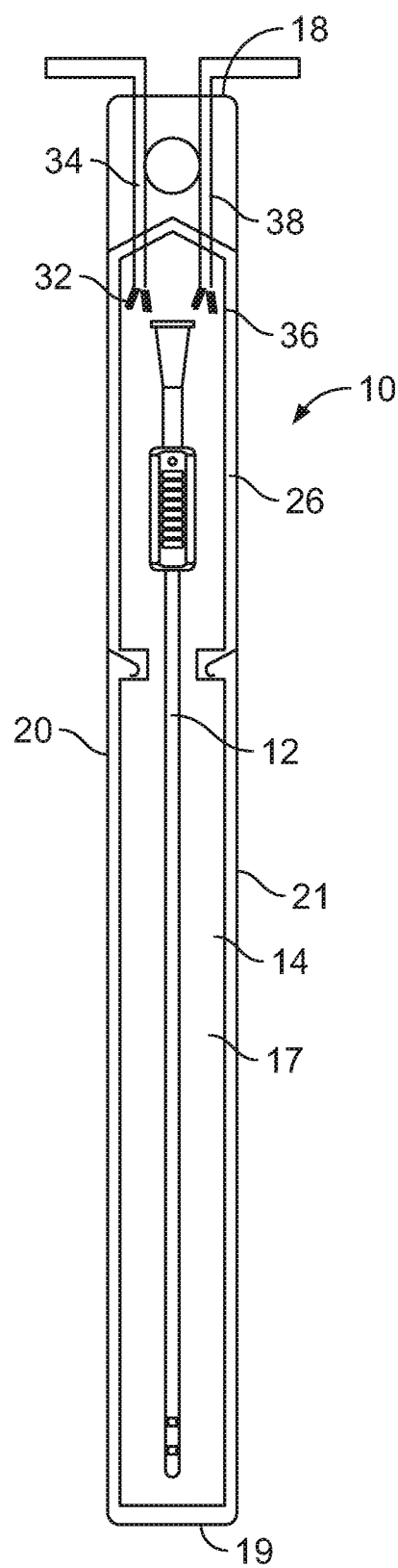
FIG. 1 is a schematic illustration of components being dispensed into a catheter package, wherein the components form a hydration solution having volatile solutes.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to a hydration medium that is a liquid hydration solution which may be used to hydrate or wet a device or product. The liquid hydration solution may be placed in a package with a device or product wherein the hydration solution directly contacts the device or product to hydrate or wet the device.

The hydration solution includes a solvent, which is a hydration liquid that hydrates the product, and a dissolved volatile solute dissolved in the hydration liquid. Volatile solutes also may impart sensory benefits (e.g. fragrance), as well and functional benefits (preservative and freeze thaw protection). The liquid may be water or any other suitable hydration liquid, and the volatile solute may be one or more gases dissolved in the liquid to form the hydration solution. In one embodiment, the hydration solution may be saturated or supersaturated with gas. The gas or other volatile solute may include one or more of carbon dioxide, nitrogen, and/or sulfur dioxide. When sulfur dioxide gas is dissolved in the hydration solution, the sulfur dioxide gas may serve as, and/or give rise to or produce non-volatile preservatives, such as sulfites.

In one alternative, the addition of sulfur dioxide to the hydration liquid (not containing sulfite salts) will result in a reduction of pH of the solution, which will provide a preservative effect. In this alternative, little or no sulfite is formed, and the sulfur dioxide gas remains as a hydrated gas and a volatile preservative.

When addition of sulfur dioxide leads to the formation of a non-volatile preservative, such preservatives may include sulfites. Such sulfites may include, for example, sodium sulphite, sodium bisulfite, sodium hydrogen sulphite, sodium metabisulfite, potassium metabisulfite, calcium sulphite, calcium bisulfite, calcium hydrogen sulphite, or potassium bisulfite. The formation and identity of the preservative formed in the solution may depend on other materials present in the formulation. For example, volatile sulfur dioxide gas and a salt may be included in the hydration liquid to generate non-volatile sulfite preservatives in the hydration liquid. Such salts may include, but are not limited to, sodium sulfite, sodium bisulfite, sodium hydrogen sulphite, sodium metabisulfite, potassium metabisulfite, calcium sulfite, calcium bisulfite, calcium hydrogen sulfite, or potassium bisulfite. The preservative may, for example, prevent decomposition of the hydrophilic coating, prevent microbial growth, maintain pH or otherwise stabilize the chemical environment within the catheter package.

The volatile solute or agent may also include a volatile oil, such as hydrocarbon volatile oils, alcoholic volatile oils, aldehyde volatile oils, phenolic volatile oils, ketonic volatile oils, phenolic ether volatile oils, oxidized volatile oils, etc. The concentration levels of the dissolved gas within the hydration liquid may be any suitable level and at times may be higher than saturation equilibrium.

As will be explained in more detail below, the hydration solution and a medical device may be packaged in a sealed gas impermeable package. The hydration solution will be under pressure within the package so that the gas remains dissolved within the hydration solution while the package is sealed. While the gas is dissolved within the hydration solution, the gas suppresses the freezing point of the hydration liquid, such that the freezing point of the hydration solution is less than that of the hydration liquid.

The gas may be dissolved in the liquid by any suitable method. For example, gas may be dosed into the package at high pressures and the package may then be sealed. Under the high pressure within the package, the gas dissolves in the liquid to form the hydration solution. In another example, reactants may be placed in the package with the liquid and the package is sealed. When the reactants react, they produce gas within the package. The reactants may be any reactants that produce a gas. For example, the reactants may be sodium bicarbonate and citric acid. The reactants may be in two separate liquids that are mixed within the package. In one embodiment, a packaging containing a medical device may receive a first liquid of water and sodium bicarbonate and a second liquid of water and citric acid. The package may then be sealed. In another embodiment, one or both of the reactants may be dispensed into the package in solid form, along with a liquid. The liquid may dissolve the solid reactants and the reactants react to form the gas. The gas increases the pressure within the package such that a portion of the gas dissolves within the liquid to form the hydration solution. When the package is opened by the user and the hydration liquid is exposed to atmospheric pressure, the gas leaves the liquid or effervesces.

The hydration solution may include other components as well, such as viscosity increasing agents, stain reducing agents, osmolality increasing agents, etc. The viscosity increasing agents, may include but are not limited to, glycerol, polyethylene glycol, sugar alcohols, polyols, sugars, soluble polymers including polysaccharides, polyvinylpyrrolidone, polyethylene oxide, cationic or anionic polyelectrolytes including polyampholytes. The hydration solution may further include a salt, such as sodium chloride. The hydration solution may comprise a polymer, such as a hydrophilic polymer. The hydrophilic polymer may be a synthetic or natural hydrophilic polymer. In one embodiment, the polymer may include polyvinylpyrrolidone. In another embodiment, the polymer may include a polysaccharide.

Figures 2, 3:
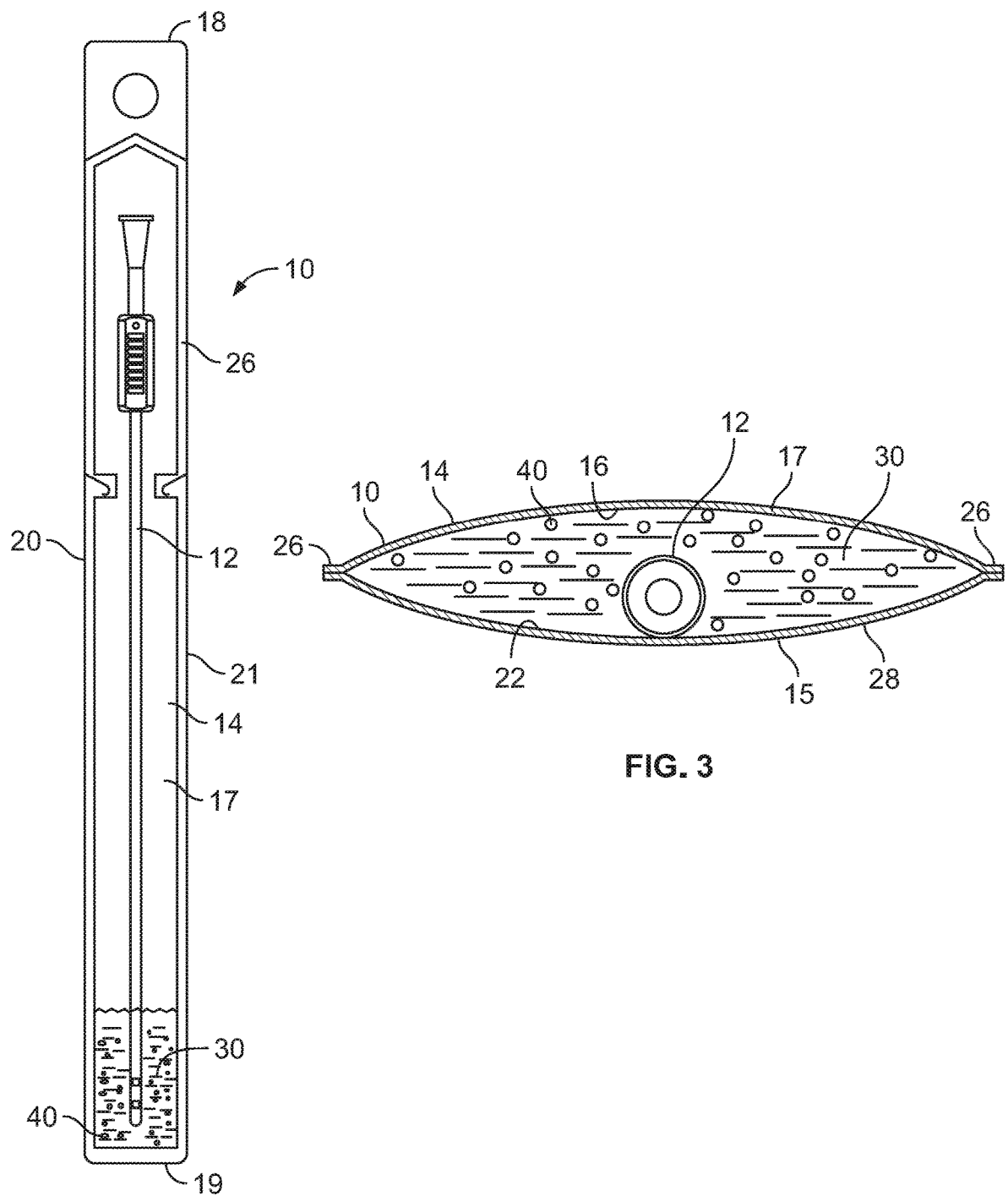
FIG. 2 is a front plan view of the catheter package of FIG. 1 showing the hydration solution within the cavity of the package.
FIG. 3 is a cross-sectional view of the package shown in FIG. 2.

Turning now to FIGS. 1-4, there is shown a medical device package 10 for containing a medical device, such as the illustrated catheter 12, and a hydration solution 30 (FIGS. 2 and 3). The hydration solution 30 may be any of the hydration solutions disclosed herein and the medical device may be any medical device. In the illustrated embodiment, the catheter may be a hydrophilic catheter.

Figure 4:
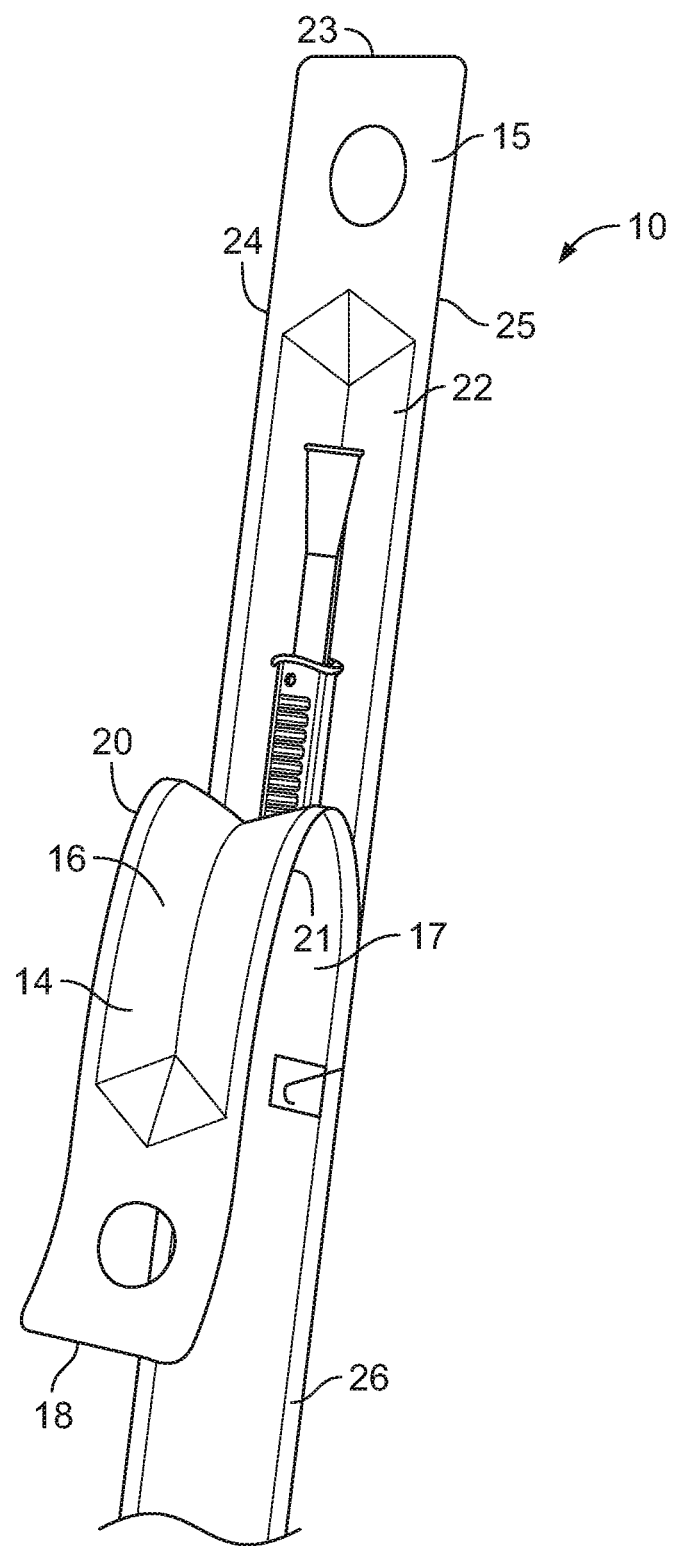
FIG. 4 is a front perspective view of the catheter package of FIG. 1 showing the package in an opened position.

The package 10 may be any suitable package for holding the device. In the illustrated embodiment, the package 10 includes a front sheet 14 and a back sheet 15 (FIGS. 2 and 3). The front sheet 14 includes an inner surface 16 facing the back sheet 15, an outer surface 17 facing the ambient atmosphere, a top edge 18, bottom edge 19 and opposed first and second side edges 20 and 21. Referring to FIGS. 3 and 4, the back sheet 15 includes an inner surface 22 facing the front sheet 14, an outer surface 28 facing the ambient atmosphere, a top edge 23, bottom edge (not shown) and opposed first and second side edges 24 and 25.

The front sheet 14 and back sheet 15 may be made from a liquid and gas impermeable material. For example, the front and back sheets 14 and 15 may be made from a polymer film and/or a metal film. In one embodiment, the material may be a polymer/metal laminate, such as a polymer/aluminum laminate.

The front sheet 14 and back sheet 15 may be sealed to each other to define a cavity for holding the catheter 12. The front sheet 14 and back sheet 15 may be sealed to each other to form a gas tight cavity. In the illustrated embodiment, the front sheet 14 and back sheet 15 are sealed to each other by a peripheral seal 26. The peripheral seal 26 may be a peelable seal that may be a heat seal, an adhesive seal or any other suitable peelable seal that allows the front sheet 14 to be separated from the back sheet 15 when the sheets are peeled apart during use.

Referring back to FIG. 1, during the manufacturing process, the hydrophilic catheter 12 is placed in the cavity of the package 10 and a first component 36 and a second component 38 for forming the hydration solution may be dispensed into the package just prior to the package being sealed. The components may be dispensed into the package through dispensing members or spouts 34 and 38, respectively. In one embodiment, the hydration solution forming components may be liquid and a volatile solute, such as a gas or oil. In another embodiment, the hydration solution forming components may be a liquid and reactants. The reactants may be liquid or dissolved in the liquids dispensed into the package, or may be solids dispensed into the package, or both liquids and solids.

For example, referring to FIG. 1, during packaging of catheter 12, a first component 32 may be a liquid containing a first reactant and the second component 36 may be a liquid containing a second reactant. After the first and second liquids are dispensed into the package, the package is sealed. When the first and second liquids mix, the first and second reactants react with each other to release a gas within the package. The gas pressurizes the package and a portion of the gas dissolves in the liquid to form hydration solution 30 (FIGS. 2 and 3). As schematically shown, a volatile solute, such as gas 40, is dissolved within the hydration solution 30. While the package is closed, the gas remains within the solution, which decreases the freezing point of the hydration solution. The hydration solution 30 may be saturated or super saturated with the gas.

In another embodiment, the first spout 34 may dispense a hydration liquid and the second spout 38 and/or a third spout may dispense solid forms of the reactants. In yet another embodiment, the first spout 34 may dispense a hydration liquid containing a first reactant and the second spout 38 may dispense the second reactant in a solid form. In yet a further embodiment, the first spout 34 may dispense a hydration liquid into the package and the second spout 38 may dispense gas at a high pressure.

Referring to FIG. 4, when the user opens the package, the pressure within the package is released. The hydration solution is exposed to atmospheric pressure and the volatile solute, such as the gas, effervesces from the solution.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A packaged urinary catheter product, comprising:
    a sealed gas impermeable package with a gas tight cavity containing:
        a hydrophilic urinary catheter; and
        a hydration medium comprising a solution including a liquid and a volatile solute dissolved in the liquid, the hydration medium being free flowing within the gas tight cavity; and
    wherein the volatile solute produces a preservative.

2. The product of claim 1, wherein the dissolved volatile solute is a gas.

3. The product of claim 2, wherein the volatile solute comprises one or more of carbon dioxide, nitrogen and sulfur dioxide.

4. The product of claim 1, wherein the preservative comprises a nonvolatile preservative.

5. The product of claim 1, wherein the preservative comprises a sulfite.

6. The product of claim 5, wherein the sulfite comprises one or more of sodium sulphite, sodium bisulfite, sodium hydrogen sulphite, sodium metabisulfite, potassium metabisulfite, calcium sulphite, calcium bisulfite, calcium hydrogen sulphite, potassium bisulfite.

7. The product of claim 2, wherein the liquid is saturated or super saturated with the gas.

8. The product of claim 1, wherein the liquid comprises water.

9. The product of claim 1, wherein the solution further includes a polyol.

10. The product of claim 9, wherein the polyol comprises glycerol.

11. The product of claim 1, wherein the solution further comprises a salt.

12. The product of claim 1, wherein the solution further comprises a hydrophilic polymer.

13. The product of claim 1, wherein the solution has a lower freezing point than the liquid.

14. The product of claim 1, wherein the hydration medium is under pressure within the sealed package so that the volatile solute remains dissolved within the hydration medium while the package is sealed.

15. A packaged urinary catheter product, comprising:
    a sealed gas impermeable package with a gas tight cavity containing:
        a hydrophilic urinary catheter; and
        a hydration medium comprising a solution including a liquid and a volatile solute dissolved in the liquid, the hydration medium being free flowing within the gas tight cavity;
    wherein the dissolved volatile solute is a gas; and
    the liquid is saturated or super saturated with the gas.

16. The product of claim 15, wherein the volatile solute comprises one or more of carbon dioxide, nitrogen and sulfur dioxide.

17. The product of claim 15, wherein the liquid comprises water.

18. The product of claim 15, wherein the solution further includes a polyol.

19. The product of claim 18, wherein the polyol comprises glycerol.

20. The product of claim 15, wherein the solution further comprises a salt.

21. The product of claim 15, wherein the solution further comprises a hydrophilic polymer.

22. The product of claim 15, wherein the solution has a lower freezing point than the liquid.

* * * * *